US012390381B2

(12) United States Patent
Barrett (10) Patent No.: US 12,390,381 B2
(45) Date of Patent: Aug. 19, 2025

(54) BED RESTRAINING APPARATUS AND METHOD OF USE THEREOF

(71) Applicant: Emily Barrett, Leeds (GB)

(72) Inventor: Emily Barrett, Leeds (GB)

(*) Notice: Subject to any disclaimer, the term of this patent is extended or adjusted under 35 U.S.C. 154(b) by 232 days.

(21) Appl. No.: 18/041,096

(22) PCT Filed: Aug. 10, 2021

(86) PCT No.: PCT/GB2021/052057
§ 371 (c)(1),
(2) Date: Feb. 9, 2023

(87) PCT Pub. No.: WO2022/034301
PCT Pub. Date: Feb. 17, 2022

(65) Prior Publication Data
US 2023/0190554 A1 Jun. 22, 2023

(30) Foreign Application Priority Data
Aug. 14, 2020 (GB) ..................... 2012698

(51) Int. Cl.
*A61G 7/05* (2006.01)
(52) U.S. Cl.
CPC ......... *A61G 7/0526* (2013.01); *A61G 7/0518* (2016.11)
(58) Field of Classification Search
CPC .... A61G 7/0507; A61G 7/052; A61G 7/0526; A61G 7/0518; A61G 7/0522; A61G 7/05; A47C 21/08; A47C 29/003; A47C 20/022; A47C 21/024; A47C 21/022; A47G 9/04; A61F 5/3776

USPC ........ 5/424, 494, 505.1, 512, 621, 663, 425, 5/658; 128/872
See application file for complete search history.

(56) References Cited

U.S. PATENT DOCUMENTS

| | | | | |
|---|---|---|---|---|
| 3,742,530 | A * | 7/1973 | Clark | A61G 7/0522 5/663 |
| 4,214,328 | A | 7/1980 | Custer et al. | |
| 4,232,415 | A | 11/1980 | Webber | |
| 5,023,967 | A | 6/1991 | Ferrand | |
| 5,044,025 | A * | 9/1991 | Hunsinger | A61G 7/052 5/663 |
| 5,153,954 | A * | 10/1992 | Ohman | A47D 15/008 5/946 |

(Continued)

FOREIGN PATENT DOCUMENTS

DE   10343617 B4   12/2005

OTHER PUBLICATIONS

International Preliminary Report in PCT/GB2021/052057, mailed Feb. 23, 2023, 8 pages.

*Primary Examiner* — Madison Emanski
(74) *Attorney, Agent, or Firm* — McKee, Voorhees & Sease, PLC (57) ABSTRACT

Bed restraining apparatus is provided including at least one bed rail protective portion for at least partly covering a surface of a bed rail in use, and at least one bed restraining portion for location over at least part of a bed in use, so as to be located between opposing sides of a bed in use and/or so as to be located between bed rails on opposing sides of a bed in use. Thee at least one bed rail protective portion is arranged so as to at least partly cover an inwardly facing side wall or side wall frame member of the bed rail in use.

15 Claims, 6 Drawing Sheets

(56) References Cited

U.S. PATENT DOCUMENTS

| | | | | |
|---|---|---|---|---|
| 5,175,897 A | * | 1/1993 | Marra, Jr. ............ | A61G 7/0524 |
| | | | | 5/663 |
| 5,450,641 A | * | 9/1995 | Montgomery ......... | A47C 21/08 |
| | | | | 5/663 |
| 5,481,772 A | * | 1/1996 | Glynn .................... | A61G 7/052 |
| | | | | 5/663 |

* cited by examiner

BED RESTRAINING APPARATUS AND METHOD OF USE THEREOF

CROSS REFERENCE TO RELATED APPLICATIONS

This is a U.S. National Phase application claiming priority to PCTGB2021052057, filed Aug. 10, 2021, which claims priority to British application no. 2012698.3, filed Aug. 14, 2020.

This invention relates to bed restraining apparatus and to a method of use thereof. Although the following description refers almost exclusively to bed restraining apparatus for use on a medical or hospital bed, it will be appreciated by persons skilled in the art that the apparatus of the present invention could be used on a non-medical bed, a baby or toddler bed, child's bed, a bed used by persons with disabilities, an elderly person's bed and/or the like.

It is known to provide bed restraining apparatus on medical or hospital beds to prevent a patient in the bed from unintentionally falling out of bed, or from getting out of bed when in a confused state or if they have reduced capabilities, as this may result in injury to the patient.

An example of a bed restraint is shown in U.S. Pat. No. 5,524,306. The bed has bed rails that run laterally on each side of the bed and the restraint is located between and attached to the opposing bed rails. The restraint includes a sheet like member that is suspended above the patient. A plurality of flaps are provided along the sides of each sheet like member to allow loops to be created for location through a top rung of the bed rails and for attachment back to the sheet like member via buttons and button holes. Problems with this type of restraint is that the patient's arms and/or legs can become entangled in the bed rails or in the attachment loops of the restraint to the bed rails. The method of attachment and detachment of the bed restraint to the bed is also fiddly and time consuming and the patient cannot be quickly and safely accessed in the event of a medical emergency.

It is also known to provide protective covers for location over side rails of hospital beds, such as for example, as shown in U.S. Pat. No. 5,557,817. However, these protective covers do not prevent a patient from getting out of bed and so do not form any kind of restraint for the patient. In addition, the protective covers can easily be removed by the patient.

It is therefore an aim of the present invention to provide bed restraining apparatus that overcomes the abovementioned problems.

It is a further aim of the present invention to provide a method of using bed restraining apparatus that overcomes the abovementioned problems.

It is a yet further aim of the present invention to provide a bed including bed restraining apparatus.

It is a yet further aim of the present invention to provide a method of using a bed including bed restraining apparatus.

According to a first aspect of the present invention there is provided bed restraining apparatus, said bed restraining apparatus including at least one bed rail protective portion for at least partly covering a surface of a bed rail in use; and at least one bed restraining portion for location over at least part of a bed in use, so as to be located between opposing sides of a bed in use and/or so as to be located between bed rails on opposing sides of a bed in use; characterised in that the at least one bed rail protective portion is arranged so as to at least partly cover an inwardly facing side wall or side wall frame member of the bed rail in use.

The present invention therefore provides the advantages of restraining an occupant in a bed while preventing an occupant of the bed from becoming entangled with the one or more bed rails on the bed or the bed restraining apparatus itself. The invention is quick and easy to use, thereby allowing rapid removal of the same in the event of a medical emergency, while at the same time preventing easy removal by the occupant of the bed on which the bed restraining apparatus is being used. The apparatus of the present invention can be easily cleaned, thereby allowing its use in both medical and non-medical settings. It is also simple and cost effective to manufacture.

Preferably a typical bed rail includes a continuous wall forming a side of a bed or includes one or more frame members forming a bed rail at the side of a bed.

Preferably the frame members or the bed rail can include any or any combination of horizontal, vertical, diagonal, angled and/or transverse frame members. For example, two or more horizontal frame members can be supported a spaced distance apart by two or more vertical or upright frame members.

In one embodiment the at least one bed rail protective portion is integrally formed with the at least one bed restraining portion.

In one embodiment the at least one bed rail protective portion is attached or detachably attached with the at least one bed restraining portion via joining means or a joining mechanism.

Preferably the joining means or joining mechanism includes any or any combination of stitching, adhesive, welding, one or more clips, ties, seams, zips, hook and loop fastening (VELCRO®), straps, buckles, inter-engaging members, poppers, press studs, magnets and/or the like.

In one embodiment the location at which the at least one bed rail protective portion is attached, detachably attached or formed with the at least one bed restraining portion is such that, when the bed restraining apparatus is fitted to a bed and bed rail in use, said location is immediately adjacent to the bed rail of the bed in use or is over at least part of the bed rail in use. Thus, in one example, a seam or join between the bed rail protective portion and the bed restraining portion can be provided immediately adjacent the bed rail or over the bed rail, such as a top or outer surface of the bed rail. This improves the aesthetic appearance of the bed restraining apparatus and reduces the chance of the seam causing discomfort to an occupant of the bed. It also reduces the likelihood of an occupant of the bed separating the portions from each other.

Preferably attachment means or an attachment mechanism are provided on or associated with the bed rail protective portion to allow attachment or detachable attachment of said portion to at least part, whole or substantially a whole of a bed or bed rail in use.

Preferably the attachment means or mechanism includes any or any combination of hook and loop attachment means (VELCRO®), one or more clips, buttons, toggles, ties, zips, straps, buckles, inter-engaging members, press studs, magnets, poppers and/or the like.

In one embodiment the attachment means are provided on part of a length or side of the bed rail protective portion. Further preferably this length or side is parallel or substantially parallel to the length of the bed and/or bed rail in use.

In one embodiment the attachment means are provided along a whole or substantially whole length or side of the bed rail protective portion. This increases the security of the attachment and prevents any loose flaps of material that could cause entanglement or discomfort for the occupant of the bed in use.

Preferably the attachment means are arranged on or associated with the bed rail protective portion so as to be located and/or accessible from an outwardly facing surface of the bed rail protective portion when located on a bed or bed rail in use (i.e. on a surface of the apparatus facing outwardly of the bed and/or bed rail in use, and preferably on a side of the bed facing outwardly of the bed and bed rail).

Preferably the attachment means are provided on or associated with the bed rail protective portion so as to be located and/or accessible at or towards a base or lower half of the bed or bed rail in use. This positioning makes it harder for a patient or occupant of the bed for which the apparatus is being used on to open the attachment means in use.

In one embodiment a cover, tab or flap is provided over and/or associated with the attachment means and/or joining means so as to further prevent an occupant of the bed from accessing the attachment means and/or joining means.

In one embodiment reflective and/or coloured means are provided on and/or associated with the attachment means, joining means or the bed rail protective portion so as to allow a carer of the occupant of the bed or medical personnel to easily locate the attachment means in case of an emergency, in the dark and/or in reduced illumination conditions.

In one embodiment at least part of the bed rail protective portion is in contact with (directly or indirectly) the side wall or side wall frame member of the bed rail and covers at least part of the inwardly facing surface of the side wall or side wall frame member of the bed rail.

Preferably the inwardly facing side wall or side wall frame member of the bed rail is an upright wall of the bed rail which is transverse, perpendicular or substantially perpendicular to the main or upper surface of the bed on which an occupant typically lies in use.

Preferably the bed rail protective portion is arranged so as to also cover a space between two or more bed rail frame members on at least one side of the bed in use and/or to at least partly cover a space between a bed rail member and a surface of the bed in use.

Preferably the bed rail protective portion is arranged so as to form a loop, cuff or sleeve surrounding a part, whole or substantially a whole of a bed rail when fitted to the bed rail in use.

Preferably the bed rail protective portion is any member that offers protection to an occupant of the bed from injuring themselves and/or entangling a part of themselves on or with a bed rail of the bed, and/or reduces or prevents any discomfort that might be caused by the bed rail to an occupant of the bed.

Preferably reference to bed rail typically means all the bed rail elements provided on one side of a bed.

Preferably the bed rail protective portion is adjustable to allow the size of the bed rail protective portion, loop, cuff or sleeve formed when in an attached position to be adjusted to fit different size and/or designs of beds and/or bed rails. It also preferably allows adjustment of the tautness of the bed restraining portion over the bed in use.

In one embodiment the attachment means and/or joining means are adjustable to allow the size of the bed rail protective portion, loop, cuff or sleeve formed to be adjusted. For example, the hook and loop fastening used to provide the attachment means and/or joining means in one example can be of such width that multiple attachment positions can be created by the same. Alternatively, more than one set of attachment means and/or joining means can be provided and a user can select one set of the plurality of sets of attachment means and/or joining means to use to allow adjustment of the size of the bed rail protective portion.

Preferably the bed rail protective portion is movable between an attached position, wherein it forms a loop, cuff or sleeve that can be engaged around at least part of a bed rail in use and is held firmly in place on the bed rail, to a detached position, wherein the bed rail protective portion can be removed from around the bed rail.

In one embodiment the bed rail protective portion is arranged to cover and contact an inwardly facing side wall surface of the bed rail when attached to the bed rail in use.

Preferably the bed rail protective portion is also arranged to cover a space between two or more bed rail members on one side of a bed in use and/or to at least partly cover a space between a bed rail member and a surface of a bed across a whole or substantially whole height of the bed rail (i.e. the distance between a base of the bed or bed rail and a top of the bed rail).

Preferably the height or side wall of the bed rail is the surface arranged transverse, perpendicular or substantially perpendicular to an upper surface of the bed (i.e. the upper surface is that surface that an occupant lies on when on the bed) when the bed rail is in an in-use position.

In one embodiment the bed rail protective portion is provided to cover an inwardly facing surface of the bed rail, a space between two or more bed rail frame members on one side of a bed in use and/or to at least partly cover a space between a bed rail member and a surface of a bed across part of a height of the bed rail (i.e. part of the distance between a base of the bed or bed rail and a top of the bed rail). Thus, unlike prior art apparatus, the bed rail protective portion prevents entanglement of a patient's limbs in any portion of the bed rail in at least the height direction of the bed rail.

Preferably the bed rail protective portion is arranged to be in direct contact with both the inwardly and outwardly facing surfaces of a bed rail (i.e. the surfaces of the bed rail facing towards the bed and away from the bed respectively).

In one embodiment cushioning means are provided on and/or associated with the bed rail protective portion to provide a cushioning effect to the bed rails in use.

In one embodiment the cushioning means are provided on and/or associated with an inwardly and/or outwardly facing surface of the bed rail protective portion. In this embodiment, the term "inwardly facing surface" can mean a surface of the bed rail protective portion facing inwardly of the bed or can mean a surface of the bed rail protective portion facing inwardly of a loop, cuff or sleeve formed by the bed rail protection portion when fitted to the bed rail in use.

The term cushioning means is defined as any means or member providing a cushioning, softening and/or shielding effect to a bed rail or item in use.

Preferably the cushioning means includes any or any combination of foam, rubber, padding, feather, pad, cushion and/or the like.

Preferably the cushioning means is joined to the bed rail protection portion, or a surface thereof, via cushion joining means, such as for example, any or any combination of adhesive, stitching, welding, location within a pocket or sleeve, hook and loop fastening (VELCRO®), one or more magnets, press studs, poppers, inter-engaging members, ties, straps, buckles and/or the like.

In one embodiment each, or at least one, of the bed rail protective portions comprises or consists of a single flap which can be detachably attached to itself and/or to a part of the bed rail restraining portion via the attachment means and/or joining means. The single flap can be moved around the bed rail to form the loop, cuff or sleeve in use.

In one embodiment each, of at least one, of the bed rail protective portions includes or consists of two, or two or more, flaps. Further preferably, a first flap for location on at least part of the outside or outwardly facing surface of the bed rail in use, and at least a second flap for location on at least part of the inside or inwardly facing surface of the bed rail in use.

Preferably the at least second flap is in direct contact with the inwardly facing surface or side wall of the bed rail when in an attached position in use.

Preferably the first flap is in direct contact with the outwardly facing surface, side frame members or side wall of the bed rail when in an attached position in use.

Preferably the two, or two or more, flaps are joined, attached or detachably attached together via the attachment means and/or joining means in use.

Preferably the at least second or inner flap is longer in length than the first or outer flap. This allows the flaps to be attached or detachably attached together on the outwardly facing side of the bed rail in use.

Preferably the bed rail protective portion and/or the flaps of the bed rail protective portion is/are hingedly or pivotally joined or formed with the bed restraining portion, thereby allowing the bed rail protective portion to be pivotally or hingedly moved relative to the bed restraining portion in use.

Preferably the bed rail protective portion, bed restraining portion and/or the flaps are flexible or substantially flexible to allow movement of the same between the attached and detached positions with respect to the bed rail and/or relative to other portions of the bed restraining apparatus in use.

In one embodiment handle means or mechanism are provided on and/or associated with the bed rail protective portion and/or bed restraining portion to allow a user to more easily grip/handle the same in use. For example, handle means in the form of one or more loops, rings, straps and/or strips can be provided to allow a user to grip/handle the same in use.

Preferably gripping means or mechanism are provided on and/or associated with the bed rail protective portion to allow gripping of said portion to the bed rails in use. The gripping means help to prevent the apparatus from sliding along or slipping on the bed rails in use, thereby maintaining the apparatus of the present invention in position on the bed in use.

Preferably the gripping means includes any or any combination of one or more gripping members, rubber, silicone, TPU material (thermoplastic polyurethane material), non-slip surface or means and/or the like.

Preferably the gripping means are provided on or associated with an inwardly facing surface of the bed rail protective portion and/or one or more flaps (i.e. a surface facing inwardly of the loop, flap, cuff or sleeve formed when the portion is fitted to a bed rail in use) or a surface coming into direct contact with the bed rails when the apparatus is fitted to the same in use.

Preferably at least two bed rail protective portions are provided with the apparatus; one bed rail protective portion provided on each of two opposing sides of the bed restraining portion. This typically allows opposing bed rails of a bed to be protected by the bed rail protective portions in use.

Preferably the, or each, of the bed rail protective portions is provided along or joined to a lateral and/or longitudinal edge of the bed restraining portion. This preferably corresponds to a lateral edge of the bed on which the apparatus is used.

In one embodiment the material of the bed rail protective portion is continuous or substantially continuous with the material of the bed restraining portion, thereby preventing any apertures or gaps therebetween that could result in patient limb entanglement in use.

Preferably the material of the bed rail protective portion and/or the material of the bed restraining portion is continuous or substantially continuous to prevent apertures or gaps therebetween that could result in patient limb entanglement in use.

Preferably the two bed rail protective portions are provided along or joined to opposing lateral and/or longitudinal edges of the bed restraining portion.

Preferably the bed rail protective portion and/or the bed restraining portion is formed from sheet or sheet like material.

Preferably the bed restraining portion is anything that can be located over at least an upper surface of a bed (i.e. the surface of the bed on which an occupant typically lies on in use) and helps to restrain an occupant of the bed from exiting the bed without first removing the bed restraining portion.

Preferably the bed restraining portion is arranged to be located a spaced distance above a base of a bed and/or upper surface of a mattress of a bed when the bed rail protective portion is fitted to the bed rails in use. Further preferably the bed restraining portion is arranged to be located a spaced distance above an individual or occupant lying in the bed in use.

Preferably the bed restraining portion is of such shape, design and/or dimensions that it is pulled taut or substantially taut between two sides and/or bed rails of the bed when fitted in use.

In one embodiment the bed restraining portion has a length or longitudinal distance that is equal or substantially equal to the length of the at least one bed rail protective portion.

In one embodiment the bed restraining portion has a length or longitudinal distance that is greater in length to the length of the at least one bed rail protective portion. This could allow, for example, a base of the bed restraining portion to be tucked under the mattress of the bed at an end of the bed in use if required.

Preferably the bed restraining portion and/or bed rail protective portion is made from approved medical material. This allows the apparatus of the present invention to be easily cleaned and to meet infection prevention control measures.

Preferably the bed restraining portion and/or bed rail protective portion is made from material that allows a user of the apparatus to regulate their body temperature in use, such as for example to have thermal insulating properties, be breathable or allow air passage therethrough and/or the like.

Preferably the bed restraining portion and/or bed rail protective portion is made from a resilient material, and further preferably a material capable of being stretched in multiple directions.

Preferably the bed restraining portion and/or bed rail protective portion is made from a waterproof or water resistant material.

Preferably the resilient material is Darlexx® made by Shawmut Corporation, or other similar warp knit fabric that is laminated to a monolithic or thermoplastic film.

Preferably the material has thermal insulating properties.

Preferably the material is a one, two or three ply Lycra based material, and further preferably includes a thermoplastic film and/or microfiber fleece therewith.

According to a second aspect of the present invention there is provided a method of using bed restraining apparatus, said bed restraining apparatus including at least one bed rail protective portion and at least one bed restraining portion, said method including the steps of covering at least part of a bed rail of a bed with the at least one bed rail protective portion; locating at least part of the at least one bed restraining portion over at least part of the bed, so as to be located between opposing sides of the bed and/or so as to be located between bed rails on opposing sides of the bed; characterised in that the at least one bed rail protective portion is arranged so as to at least partly cover an inwardly facing side wall or side wall frame member of the bed rail in use.

According to a further aspect of the present invention there is provided a bed including bed restraining apparatus.

Preferably the bed includes a bed frame and one or more bed rails provided along at least one lateral edge of the bed frame.

Preferably a mattress is supported on the bed frame in use.

According to a yet further aspect of the present invention there is provided a method of using a bed including bed restraining apparatus.

It will be appreciated that the bed restraining apparatus of the present invention is particularly useful on the beds of elderly, infirm or frail individuals who may inadvertently injure themselves if they fall out of bed or try to get out of bed unaided. The present invention is also useful for individuals for example with cognitive difficulties, such as dementia, brain injuries, reduction in awareness, individuals with head injuries, stroke patients, patients with extensive injuries or who have undergone surgery who are unable to tolerate bedding placed on them directly, children or adults who sleep walk and/or the like. It is noted that the above list is a non-exhaustive list of possible uses and applications of the present invention.

The present invention can be used to keep individuals safe whilst they are asleep or in bed. It provides reassurance and respite to carers, parents of young children, service providers and health care workers. The present invention can reduce the risk of falls of individuals and can act as a gentle reminder to individuals to remain in bed, while still allowing the individual to have some freedom of movement within the bed.

The present invention also helps individuals with poor dexterity, control of movement of involuntary movements from becoming trapped between the bed rails of a bed. The bed restraining portion that provides a cover over the top of the bed decreases the risk of an individual user straddling the bed rails, thereby providing safety and comfort with minimal management intervention. It also allows an individual to maintain their dignity as much as possible and to promote the concept of dignity in care.

The present invention allows carers to continue to care for their loved ones and carry out their activities of daily living with the peace of mind that their loved ones are safe in their own bed.

Embodiments of the present invention will now be described with reference to the following figures, wherein.

It will be appreciated by persons skilled in the art that the bed restraining apparatus of the present invention can include any combination of features shown in any of the different illustrated embodiments.

Figures 1, 2, 3:
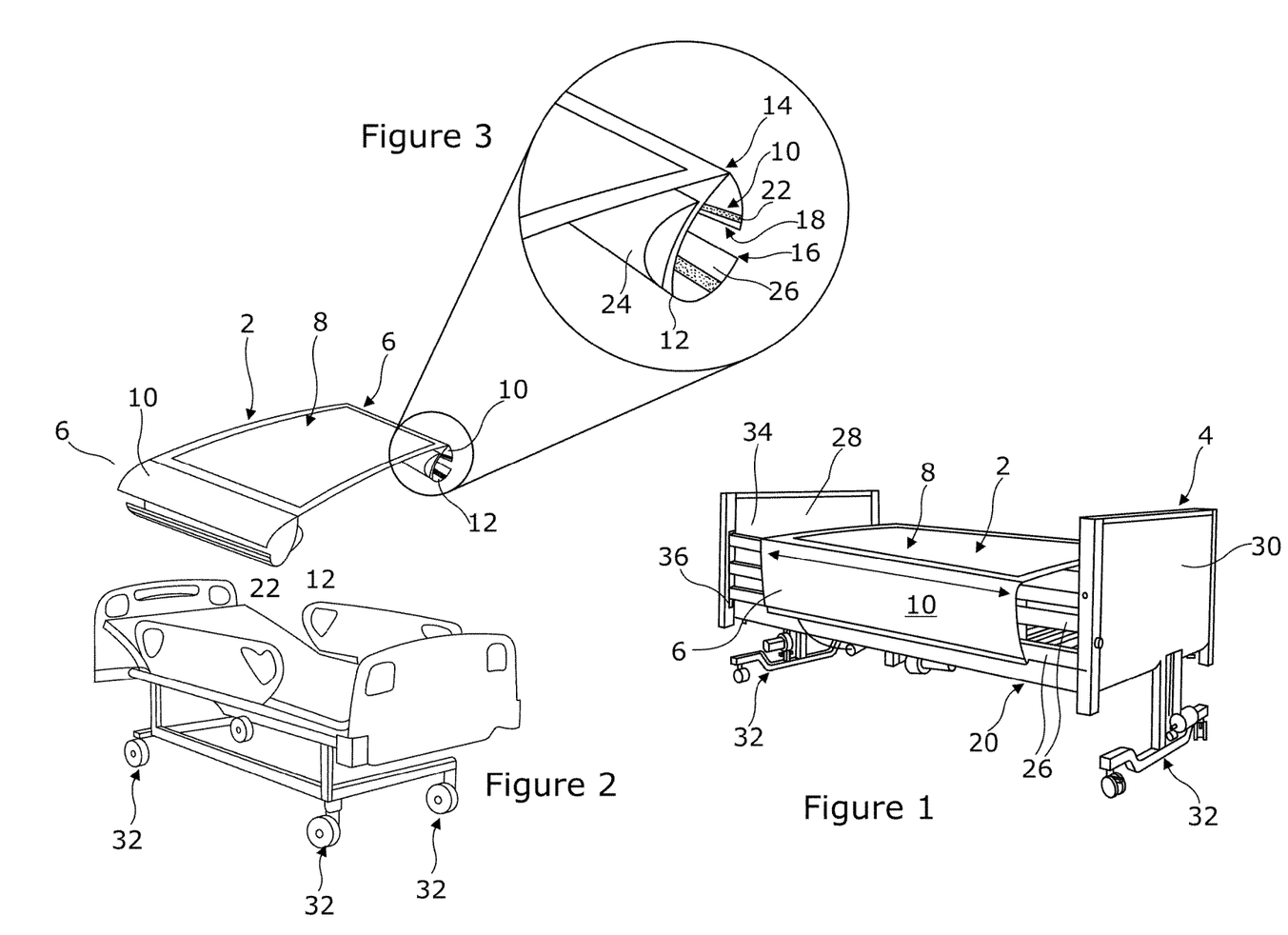
FIG. 1 is a perspective view of bed restraining apparatus according to an embodiment of the present invention fitted to a bed in use.
FIG. 2 is an exploded view of bed restraining apparatus according to an embodiment of the present invention and a bed that the apparatus can be fitted to in use.
FIG. 3 is an enlarged view of part of the bed restraining apparatus shown in FIG. 2.
Figure 4:
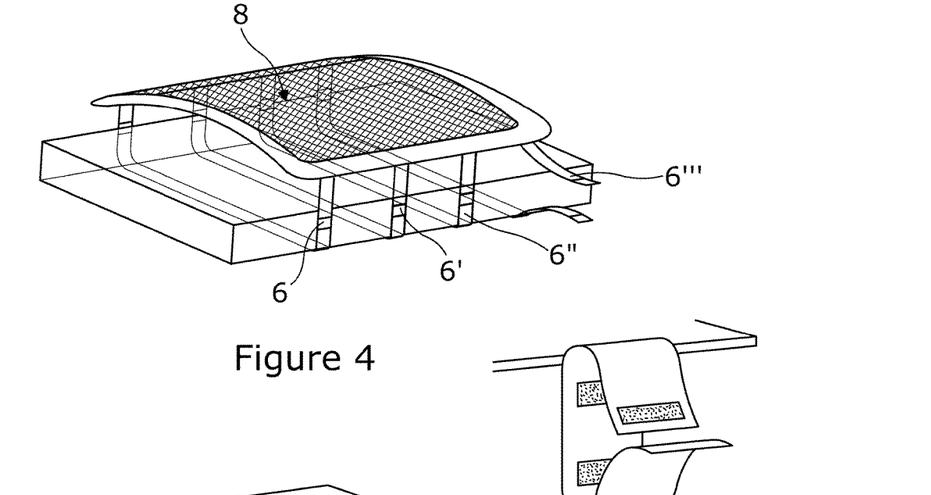
FIG. 4 is a perspective view of bed restraining apparatus according to a further embodiment of the present invention.
Figure 5A:
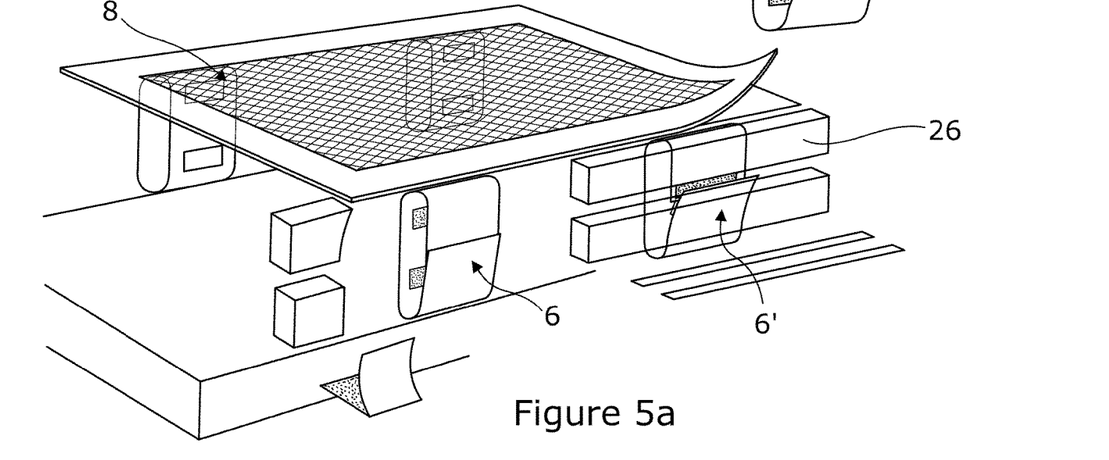
FIG. 5a is a yet further embodiment of bed restraining apparatus according to an embodiment of the present invention.
Figure 5B:
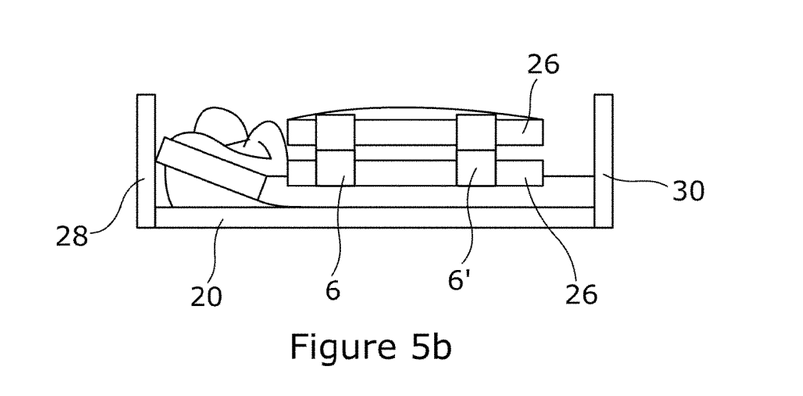
FIG. 5b is a side view of the bed restraining apparatus in FIG. 5a being used on a bed with a patient in the bed.
Figure 6:
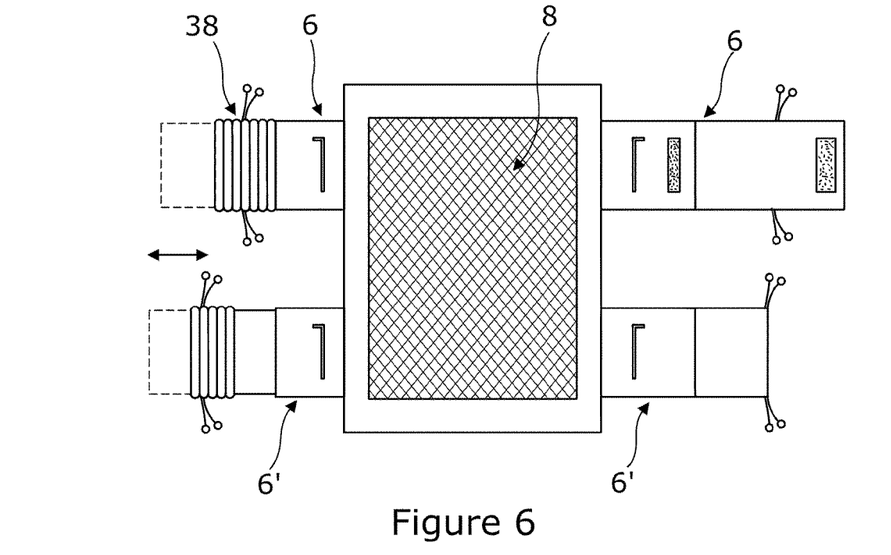
FIG. 6 is a plan view of bed restraining apparatus according to an embodiment of the present invention.
Figure 7:
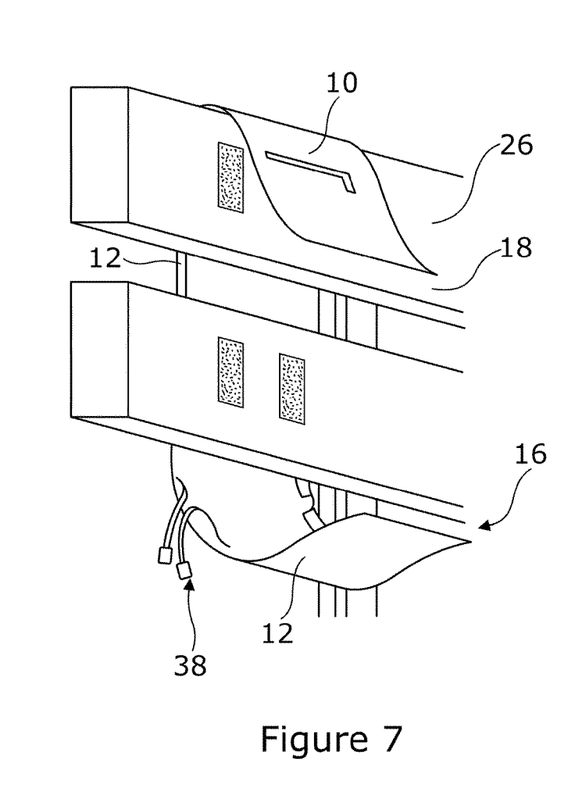
FIG. 7 is an enlarged view of a bed rail protection portion according to one embodiment of the present invention.
Figure 8:
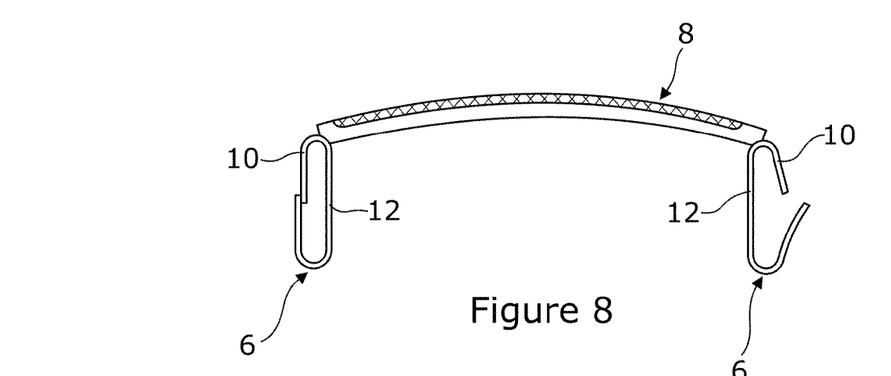
FIG. 8 is an end view of the bed restraining apparatus shown in FIGS. 6 and 7.

Referring firstly to FIGS. 1-3, there is illustrated bed restraining apparatus 2 according to an embodiment of the present invention. Although the apparatus is shown for use with a medical type of bed 4, it will be appreciated that the bed restraining apparatus 2 could be fitted to any type, size and/or design of bed.

The bed restraining apparatus 2 includes two bed rail protection portions 6; each portion 6 located on opposing sides of a bed restraining portion 8.

Each bed rail protection portion 6 includes a first outer flap 10 and a second inner flap 12. Both the first outer flap 10 and the second inner flap 12 are flexible and can pivot with respect to the bed restraining portion 8 to which the flaps are joined to or integral with. This allows easy manipulation of the flaps with respect of the bed restraining portion 8 in use.

The second inner flap 12 in the illustrated example has a greater width 'w' (i.e. the distance from the join 14 with the bed restraining portion 8 to the free end 16 opposite the join) than the first outer flap 10 "w1" (i.e. the distance from the join 14 with the bed restraining portion 8 to the free end 18 opposite the join). This allows attachment between the first outer and second inner flaps 10, 12 to take place on the outwardly facing surface of the bed restraining portion (i.e. the surface facing outwardly of the bed), and preferably near or adjacent a base 20 of the bed 4. The positioning of the attachment between the flaps 10, 12 reduces the likelihood of an individual being restrained by the apparatus 2 from accessing the attachment themselves, while allowing quick and easy access for a carer or medical personnel in the event of an emergency or medical emergency.

Attachment means in the form of hook and loop fastenings (VELCRO®) 22 are provided on the first outer and second inner flaps 10, 12 to allow attachment of the flaps together in use. In particular, in the illustration, the fastenings 22 are provided on an inner surface of the first outer flap 10 and on an outer surface of the second inner flap 12. However, the fastenings 22 could be provided on either surface of the first outer and second inner flaps 10, 12 to allow engagement between the same in use. The dimensions of the hook and loop fastening 22 can be such that multiple attachment positions can be achieved, thereby allowing the flaps to fit a variety of different bed rail designs in use.

The first outer flap 10 and the second inner flap 12 (and thus the bed rail protection portion 6) can be moved between an attached position, wherein the free ends 16, 18 of the flaps 10, 12 are brought towards each other and engaged via the hook and loop fastenings 22 to form a loop, cuff or sleeve around the bed rails 26 on one side of the bed, as shown in FIG. 1) to a detached position, wherein the free ends 16, 18 of the flaps 10, 12 are moved away from each other and the fastenings are not engaged to allow removal from the bed rails 26, as shown in FIG. 2.

Cushioning means are provided on an inwardly facing surface of the bed rail protection portion 6 to allow a user to be cushioned from the bed rails. In the illustration, the cushioning means includes a cushioned pad 24 located on a surface of the second inner flap 12 that is to face inwardly of the bed 4 when the apparatus 2 is attached to the bed 4 in use. However, other cushioning arrangements could be provided.

Gripping means in the form of a non-slip surface 26 is provided on the surfaces of the bed rail protection portion that come into direct contact with the bed rails 26 of the bed 4 in use. This prevents the bed rail protection portion from moving along the bed rails in use and maintaining the position of the apparatus once secured to the bed.

In the illustrated example, the bed rail protection portions 6 are of equal length "1" to the bed restraining portion 8. However, it will be appreciated they can be different lengths, as shown in the embodiments described below.

The bed restraining portion 8 is formed from a sheet material that is flexible and is resilient to allow it to be pulled relatively taut between bed rails 26 on opposite sides of the bed 4 when fitted in use. The bed restraining portion 8 is also formed from a material that allows it to be easily cleaned, is waterproof, has thermal insulating properties and/or the like. This allows the apparatus 2 of the present invention to be used in a medical setting, is hygienic to use and allows regulation of the user's body temperature when the user is located on the bed under the apparatus 2 in use. In one example, the bed restraining portion 8 is formed from Darlexx®.

Medical beds 4 differ in their size, shape and design and the bed restraining apparatus 2 is adapted to fit a wide variety of medical beds and other bed types. For example, a typical medical bed 4 includes a base 20, a head board 28 located at a top end of the bed 4 and a foot board 30 located at an end opposite to the same. The base 20 of the bed 4 may or may not be attached to wheels 32 to allow easy movement of the bed 4 in use. Bed rails 26 are provided on opposing sides of the bed 4 between the head board 28 and the foot board 30. A longitudinal axis of the bed rails 26 is typically parallel to a longitudinal axis of the bed and mattress.

In use, a patient would be laid on the bed 4 with their head adjacent the head board 28 and their feet towards the foot board 30. The bed restraining apparatus 2 can be fitted to the bed 4 once the patient is in bed. The second inner flap 12 of a bed rail protection portion 6 is located adjacent an inwardly facing surface of the bed rails 26 such that the join 14 between the flap 12 and the bed restraining portion 8 is at the top 34 of the bed rails 26 and the free end 16 of the flap 12 is inserted underneath the base 36 of the bed rails 26. The first outer flap 10 of the bed rail protection portion 6 is located adjacent an outwardly facing surface of the bed rails 26 and the free end 18 of the same is moved towards the flap 12 to allow engagement of the fastenings 22 provided on both flaps 10,12. The bed restraining portion 8 is then laid across the bed 4 and over the patient between the two opposing bed rails 26 on each side of the bed. The bed restraining portion 8 is pulled taut between the two opposing bed rails 26 and the opposing bed rail protection portion 6 is attached to the bed rail. With the apparatus 2 fitted to the bed 4, the bed restraining portion 8 is typically a spaced distance above the patient, thereby allowing the patient freedom of movement and allowing them to regulate their body temperature. The cushioning pad 24 protects the patient from knocking into the bed rails 26 and injuring themselves. The bed rail protection portion 6 prevents the patient from getting their limbs entangled in the bed rails.

In some bed designs, the bed rails 26 are substantially continuous members, as shown in FIG. 2. However, the apparatus 2 of the present invention can fit to the same in a similar manner to that described above.

In the embodiments of the present invention illustrated in FIGS. 4-8, it can be seen that the bed rail protection portion does not need to extend the entire length of the bed rails 26. The same reference numerals referred to in FIGS. 1-3 are used to describe similar features in FIGS. 4-8. For example, in FIGS. 4-8, a number of bed rail protection portions 6, 6', 6", 6'" are provided on each side of the bed to connect to one side of bed rails 26. The bed rail protection portions 6-6" are provided a spaced distance apart along the length of the bed restraining portion 8. The bed rail protection portions 6-6'" can be similar in form to those shown in FIGS. 1-3.

Adjustment means in the form of a drawstring mechanism 38 can be provided on the first and/or second flaps 10, 12 to allow the length of the flaps 10, 12 to be adjusted to fit different size and/or designs of bed rails.

Thus, it can be seen that the present invention reduces the need for hand on manual moving and handling of an individual being cared for, thereby reducing the risk of injury posed to both the individual and carer. It encourages the individual to have a more peaceful night sleep. It allows individuals to stay in their own home and be cared for longer than may otherwise be the case if the present invention was not used. The present invention is less intrusive and restrictive to the individual user compared to other restraining apparatus on the market. It promotes safety by reducing the risk of limb entrapment, falls, slipping or rolling off the bed and/or the like. The present invention can help to promote independence of the user and improve their mental health and wellbeing. It reduces the requirement for 1:1 night carers, offers reassurance to both patients and carers about the patient's well-being and risk of injury and it promotes the maintenance of dignity in care. Furthermore, the present invention is easy to use and adaptable for use with different bed and/or bed rails designs.

Figures 9A, 9B:
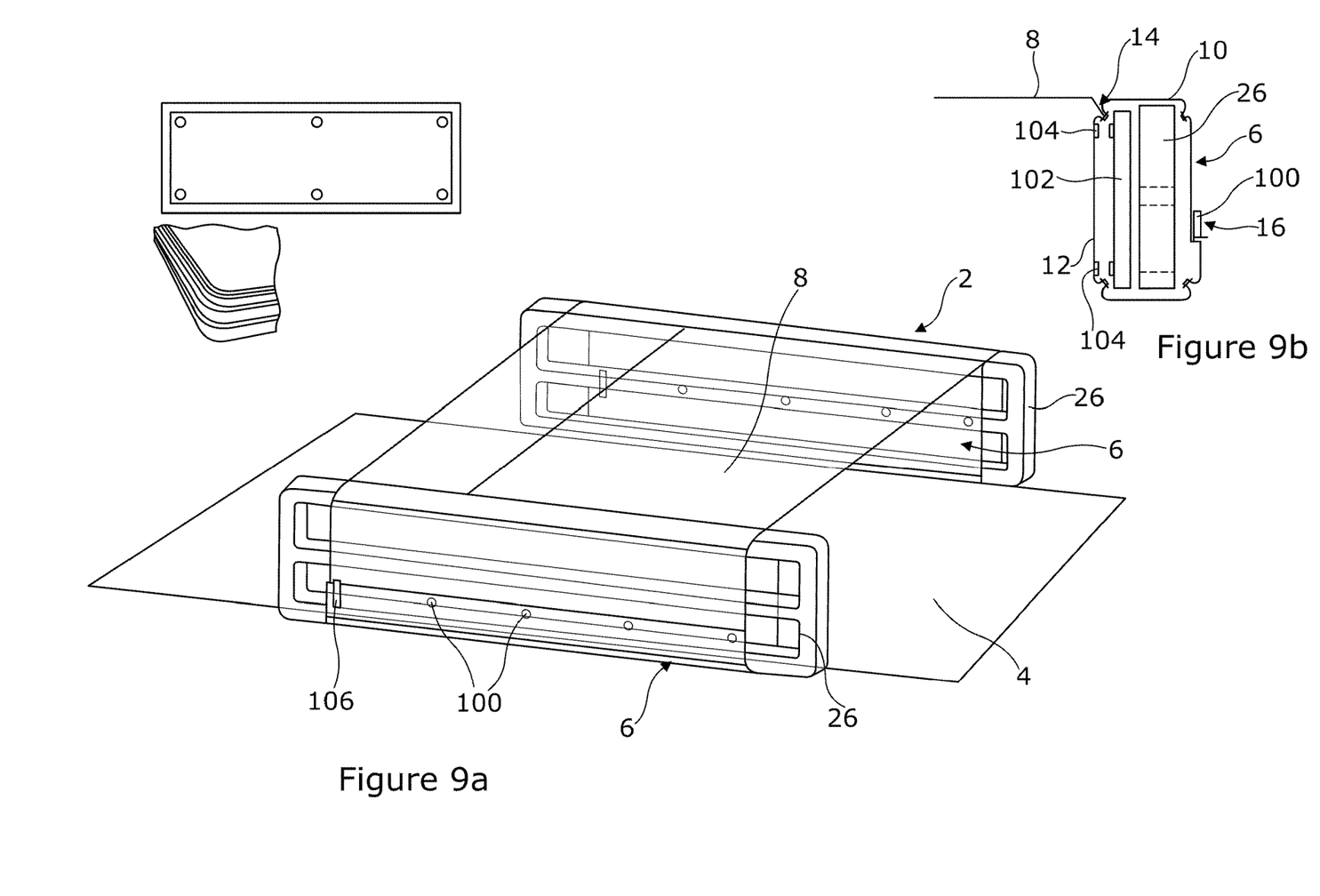
FIGS. 9a and 9b show a perspective view of bed restraining apparatus according to one example and a cross sectional view taken through the bed restraining apparatus respectively.

In FIGS. 9a-9b, an alternative embodiment of bed restraining apparatus 2 according to present invention is shown. In this example, attachment means in the form of magnets 100 are provided adjacent the free edges of the first inner flap 12 and second outer flap 10 to allow detachable attachment of the bed rail protective portion around the bed rail 26 in use. The magnets 100 are accessible on an outwardly facing surface of the bed protective portion and face outwardly of the bed when the apparatus is in position on the bed rail in use. A cushioning pad 102 is joined to the first inner flap 12 by press studs 104 (but other securing means could be used as required). The first and second flaps 12, 10 create a protective sleeve around the bed rail when attached around the bed rail in use. The cushioning pad 102 directly contacts the inwardly facing side wall of the bed rail 26. Coloured webbing 106 is provided adjacent the attachment edges of the bed protective portion to allow a carer to easily locate the same.

Figures 10A, 10B:
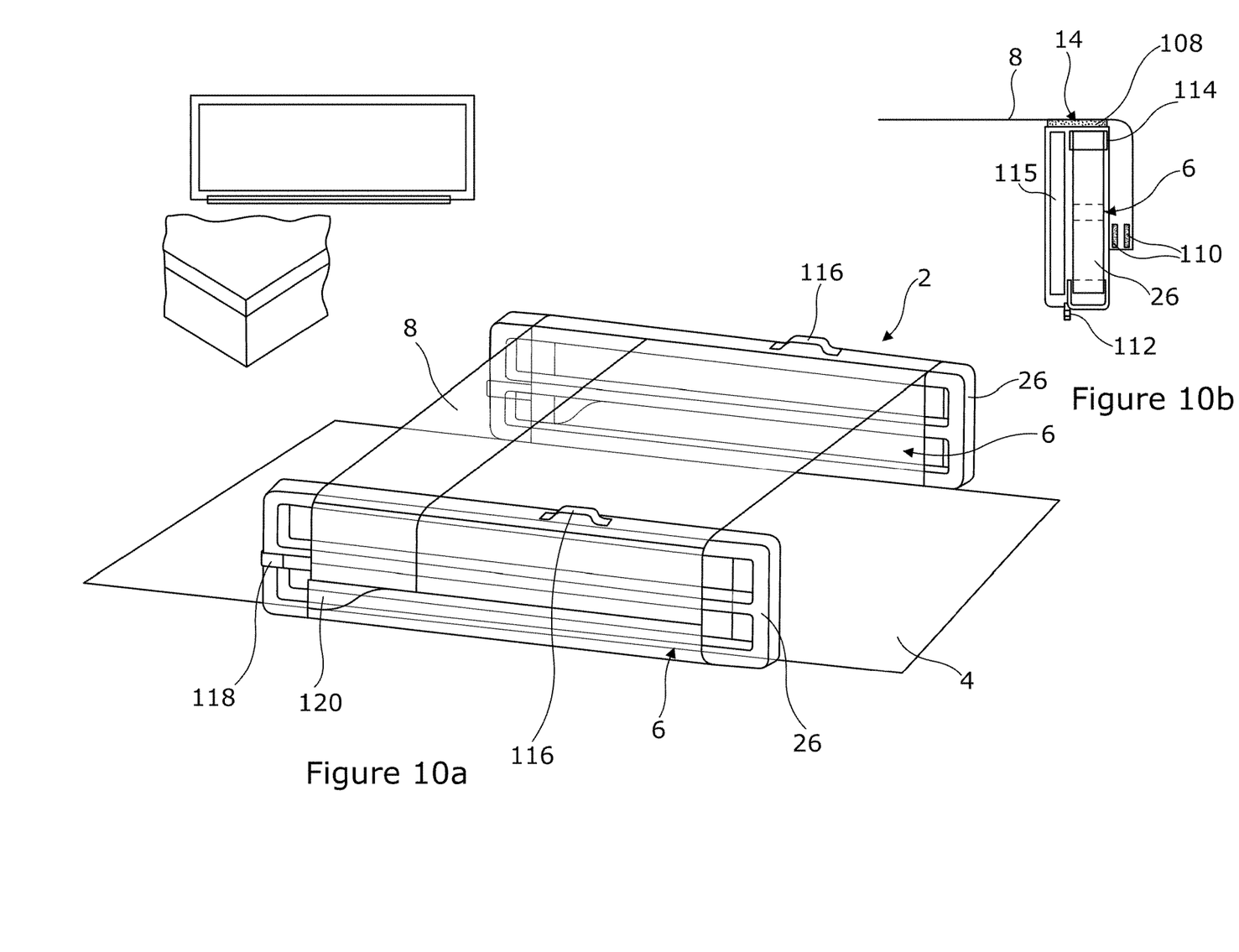
FIGS. 10a and 10b show a perspective view of bed restraining apparatus according to a further example and a cross sectional view taken through the bed restraining apparatus respectively.

FIGS. 10*a*-10*b* show a further embodiment of bed restraining apparatus 2 according to the present invention. In this embodiment, the bed rail protective portion 6 is detachably joined to the bed restraining portion 8 via a first set of hook and loop fasteners 108 positioned adjacent the top of the bed rails and a second set of hook and loop fasteners 110 positioned on the outwardly facing side walls of the bed rail. The bed rail protective portion comprises first and second flaps that are detachably attached around the bed rail 26 via attachment means in the form of a zip 112. Cushioning means in the form of a foam pad 115 is attached to an inner surface of one of the flaps to cushion the bed rail 26 from the occupant. Gripping means in the form of silicone or TPU material 114 is provided on one of the flaps inner surfaces to prevent the portion 6 from slipping on the bed rails in use. A handle 116 is provided on the bed restraining portion 8 to improve the ease of removing the portion 8 in use. Additional attachment means in the form of removable straps 118 can be used to secure the bed rail protective portion to the bed rail in use. A coloured tab 120 is provided adjacent the hook and loop fastening 110 to allow a carer to easily locate the hook and loop fastening.

Figure 11A:
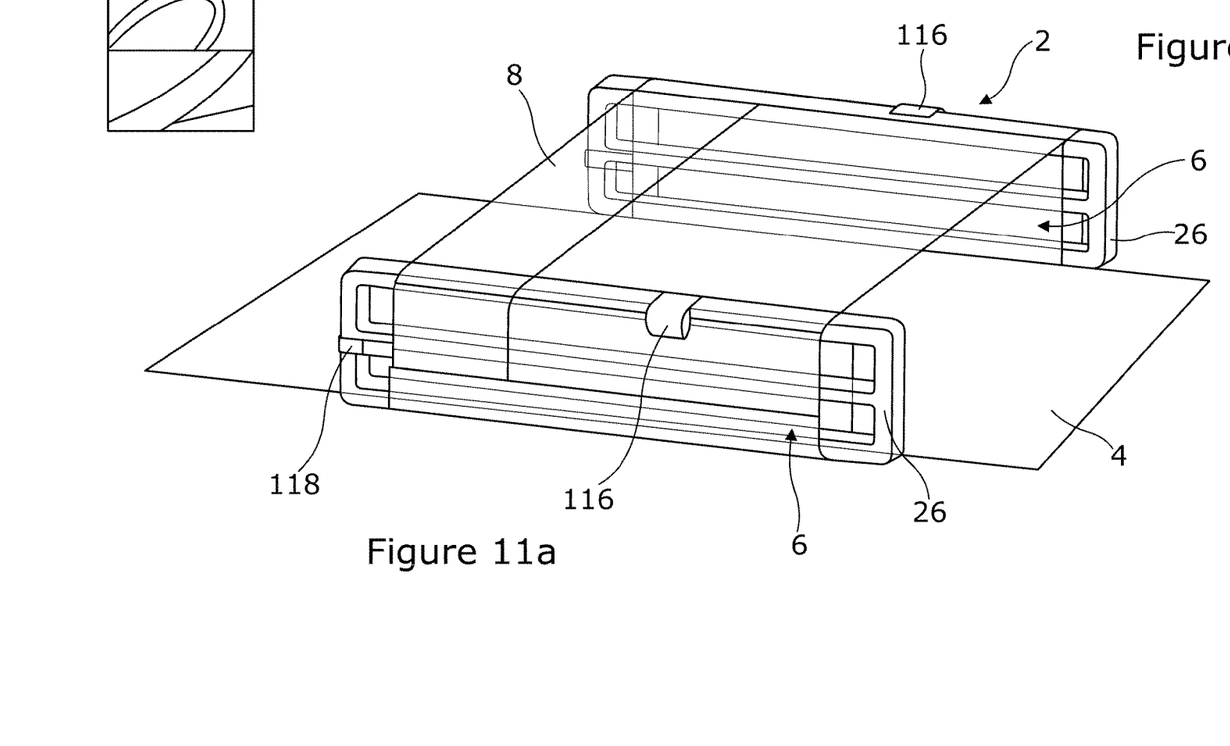
FIGS. 11a and 11b show a perspective view of bed restraining apparatus according to a yet further example and a cross sectional view taken through the bed restraining apparatus respectively.
Figure 11B:
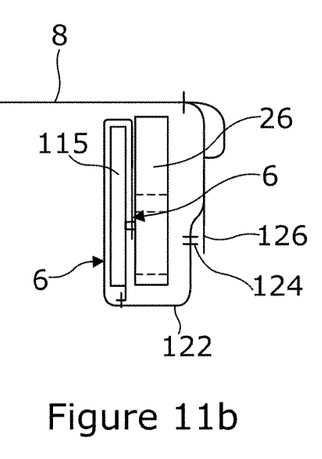

FIGS. 11*a*-11*b* show a yet further embodiment of bed restraining apparatus 2 according to the present invention. In this embodiment the bed restraining portion is of sufficient length to pass over the top and at least part of one of the outer side walls of the bed rail 26. The bed rail protective portion 6 includes a sleeve member located in contact with the inwardly facing side wall of the bed rail 26. A foam pad 115 is provided in the sleeve member to cushion the bed rails from the occupant. A flap 122 forming part of the bed rail protective portion extends below the base of the bed rail 26 and detachably attaches to the bed restraining portion via a zip 124. A cover or tab 126 is provided over the zip 124 to prevent the occupant of the bed from unzipping the zip.

The fabric of the bed restraining apparatus can be washed if required. The cushioning means can be removed to allow washing if required.

The invention claimed is:

1. A bed restraining apparatus for restraining an occupant in a bed wherein said bed restraining apparatus including at least one bed rail protective portion which is arranged to at least partly cover an inwardly facing side wall surface or side wall frame member surface of a first and second bed rail along either side of the bed; wherein attachment means are provided on or associated with the bed rail protection portion to allow detachable attachment of the bed rail protection portion to at least a part or a whole of the first and second bed rail; and wherein the attachment means are arranged so as to be located on an outwardly facing surface of the bed rail protective portion; the bed restraining apparatus further including at least one bed occupant restraining portion for location over at least a part of the bed for restraining the occupant in the bed; the at least one bed occupant restraining portion arranged such that when the at least one bed rail protection portion is fitted to the first and second bed rails, the at least one bed occupant restraining portion is located a spaced distance above an upper surface of the bed and the occupant lying in the bed and is located between opposing sides of the bed and is located between the first and second bed rails on opposing sides of the a bed; wherein the at least one bed rail protective portion is attached or detachably attached with the at least one bed occupant restraining portion via joining means or integrally formed with the at least one bed occupant restraining portion; wherein a location at which the at least one bed rail protective portion is attached, detachably attached or formed with the at least one bed restraining portion is such that when the bed restraining apparatus is fitted on the bed and first and second bed rail, wherein the location of attachment for the at least one bed rail protective portion is immediately adjacent to the first and second bed rail of the bed, and is over at least part of the first and second bed rail.

2. The bed restraining apparatus according to claim 1 wherein a cover, tab or flap is provided over and associated with the attachment means or joining means.

3. The bed restraining apparatus according to claim 1, wherein the bed rail protective portion is arranged se as to form a loop, cuff or sleeve surrounding a part, whole or substantially a whole of the first and second bed rails when fitted to the first and second bed rails.

4. The bed restraining apparatus according to claim 1, wherein cushioning means are provided on and associated with the bed rail protective portion to provide a cushioning effect to the first and second bed rails.

5. The bed restraining apparatus according to claim 1 wherein each, or at least one, of the bed rail protective portions comprises of a single flap which is configured to be detachably attached to said each, or at least one, bed rail protective portions or to a part of the bed occupant restraining portion via the attachment means or joining means.

6. The bed restraining apparatus according to claim 1, wherein each, or at least one, of the bed rail protective portions comprises or consists of two or more flaps; a first flap for location on at least part of the outwardly facing surface of the first and second bed rails, and at least a second flap for location on at least part of the inwardly facing surface of the first and second bed rails.

7. The bed restraining apparatus according to claim 6, wherein the second flap is longer in length than the first flap to allow the first and second flaps to be attached or detachably attached together on an outwardly facing side of the first and second bed rails.

8. The bed restraining apparatus according to claim 1, wherein a handle is provided on or associated with the bed rail protective portion or bed occupant restraining portion to allow the occupant or a caregiver to easily grip or handle the first and second bed rails; and wherein a non-slip surface is provided on or associated with the bed rail protective portion to prevent slipping of the bed rail protective portion on the first and second bed rails.

9. The bed restraining apparatus according to claim 1, wherein a material of the bed rail protective portion is continuous or substantially continuous with material of the bed occupant restraining portion to prevent any apertures or gaps therebetween that could result in patient limb entanglement.

10. The bed restraining apparatus according to claim 1, wherein the bed rail protective portion or the bed occupant restraining portion is formed from sheet or sheet like material.

11. The bed restraining apparatus according to claim 1, wherein the bed occupant restraining portion has a length that is equal to or greater than the length of the bed rail protective portion; or is made from a material that allows any or any combination of the occupant to regulate any of the following properties: body temperature, thermal insulation, material properties including resiliency, waterproof, or water resistance, air passage therethrough, or is a one, two or three ply elastic polyurethane fiber or fabric.

12. A method of using bed restraining apparatus for restraining an occupant in a bed, said bed restraining apparatus including at least one bed rail protective portion and at least one bed occupant restraining portion, attachment means are provided on or associated with the bed rail protection portion and arranged so as to be located on an outwardly facing surface of the bed rail protective portion, said method including steps of detachably attaching the at least one bed rail protection portion to at least part of a first and second bed rails along either side of the bed so as to at least partly cover an inwardly facing side wall surface or side wall frame member surface of the first and second bed rails; and locating at least part of the at least one bed occupant restraining portion a spaced distance above at least an upper surface of the bed and the occupant lying in the bed, so as to be located between opposing sides of the bed and/or so as to be located between bed rails on opposing sides of the bed.

13. The bed restraining apparatus according to claim 1, wherein the attachment means are configured to inter-engage by any of the following: hook and loop fasteners, magnets, zips, straps, buttons, toggles, ties, buckles, press studs, poppers, or clips.

14. The bed restraining apparatus according to claim 1, wherein the joining means are configured to inter-engage by any of the following: stitching, welding, clips, ties, seams, zips, hook and loop fasteners, straps, buckles, poppers, press studs, or magnets.

15. The bed restraining apparatus according to claim 1, wherein the cushioning means are configured to be of any of the following: foam, rubber, padding, feather, pad, or cushion.

* * * * *

UNITED STATES PATENT AND TRADEMARK OFFICE
CERTIFICATE OF CORRECTION

PATENT NO. : 12,390,381 B2
APPLICATION NO. : 18/041096
DATED : August 19, 2025
INVENTOR(S) : Emily Barrett It is certified that error appears in the above-identified patent and that said Letters Patent is hereby corrected as shown below:

In the Claims

In Claim 3, Column 12, Line 15:
DELETE: "se as"

Signed and Sealed this
Fourteenth Day of October, 2025

John A. Squires
*Director of the United States Patent and Trademark Office*